United States Patent
Narasimhan et al.

(10) Patent No.: US 7,189,386 B2
(45) Date of Patent: Mar. 13, 2007

(54) METHOD AND COMPOSITIONS FOR BLEACHING HAIR

(75) Inventors: Saroja Narasimhan, Matawan, NJ (US); Lou Ann Christine Vena, Scotch Plains, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 11/341,315

(22) Filed: Jan. 26, 2006

(65) Prior Publication Data

US 2006/0269492 A1 Nov. 30, 2006

Related U.S. Application Data

(60) Provisional application No. 60/684,766, filed on May 26, 2005.

(51) Int. Cl.
*A61K 8/00* (2006.01)
*A61K 8/64* (2006.01)

(52) U.S. Cl. .................. 424/62; 424/70.14
(58) Field of Classification Search .............. 424/62, 424/70.14
See application file for complete search history.

(56) References Cited

U.S. PATENT DOCUMENTS

| | | | | |
|---|---|---|---|---|
| 4,226,852 A | 10/1980 | Tesmann | ...... | 424/62 |
| 4,507,278 A | 3/1985 | DeMarco | ...... | 424/62 |
| 5,575,989 A | 11/1996 | Caskey | ...... | 424/62 |
| 5,674,476 A | 10/1997 | Clausen | ...... | 424/62 |
| 5,888,484 A | 3/1999 | Schmitt | ...... | 424/62 |
| 5,891,423 A | 4/1999 | Weeks | ...... | 424/62 |
| 5,964,226 A | 10/1999 | Sobel | ...... | 132/108 |
| 5,989,530 A | 11/1999 | Lorenz | ...... | 424/62 |
| 6,238,653 B1 | 5/2001 | Narasimhan | ...... | 424/62 |
| 6,315,989 B1 | 11/2001 | Narasimhan | ...... | 424/62 |
| 6,613,311 B2 | 9/2003 | Imperial | ...... | 424/62 |
| 6,703,004 B2 | 3/2004 | Narasimhan | ...... | 424/62 |
| 6,872,228 B1 | 3/2005 | Lenzi-Brangi | ...... | 8/110 |
| 7,001,593 B2 | 2/2006 | Narasimhan | ...... | 424/62 |
| 2002/0139957 A1 | 10/2002 | Matsuo | ...... | 252/186.1 |
| 2003/0206877 A1 | 11/2003 | Lenzi-Brangi | ...... | 424/62 |

OTHER PUBLICATIONS

Cab-O-Sil® Treated Fumed Silicas Overview. May 4, 2005.
Cab-O-Sil® TS-720. Treated Fumed Silica. 2002.
Cab-O-Sil® TS-610. Treated Fumed Silica. 2002.
Cab-O-Sil® TS-530. Treated Fumed Silica. 2002.
Herbal Essences® Bleach Blonding. Package Copy. Jan. 1, 2000.
Clairol® Maxi Blonde. Package Copy. Jan. 1, 2000.
Frost & Glow Dramatic All Over Bleach Blonde Kit. May 15, 2001.
Garnier Nutrisse Lightening Kit. Package Copy. Jan. 1, 2000.
Feria. The New Language of Color. Jan. 1, 2000.
Clairol XtremeFX. Package Copy. Jan. 1, 2000.
Robbins, Clarence R., Chemical and Physical Properties Behavior of Human Hair, Chapter 4, Bleaching Human Hair, pp. 67-79. Dec. 2001.
Society of Cosmetic Chemists Monograph. Permanent Hair Dyes. 1996.
Journal of Society of Cosmetic Chemistry. Vol. 36, pp. 319-333. (Sep./Oct. 1985). Using Solublity Parameters in Cosmetics Formulation.
Grulke, Eric A., Solubility Parameter Values, vol. VII, pp. 519-557. Jan. 1, 2000.
Cosmetics and Toiletries. Vol. 103, pp. 47-69. Solubility Effects in Product, Package, Penetration, and Preservation. Oct. 1988.
Mohile, R.B. Hair Care: Benefit of Coconut Oil Relevance to Hair Damage. Part III. Journal of Cosmetic Science. Vol. 50, Nov./Dec. 1999.

*Primary Examiner*—James Wilson
*Assistant Examiner*—MLouisa Lao
(74) *Attorney, Agent, or Firm*—Julie Balckburn

(57) ABSTRACT

A hair bleach mixture obtained by combining an aqueous oxidizing agent composition and a persulfate composition comprising at least one hydrophobically modified particulate, said hydrophobically modified particulate being present in the mixture in an amount sufficient to reduce diffusion and/or migration of the mixture from the hair strands to which it is applied; and a method and kit for bleaching hair.

14 Claims, No Drawings

METHOD AND COMPOSITIONS FOR BLEACHING HAIR

RELATED APPLICATION DATA

This application claims priority from provisional patent application Ser. No. 60/684,766, filed May 26, 2005.

TECHNICAL FIELD

The invention is in the field of methods and compositions for bleaching hair.

BACKGROUND OF THE INVENTION

Women have been bleaching their hair for thousands of years. Some of the primitive concoctions used to bleach hair in early Rome, prior to the beginning of the Christian era, included native minerals such as alum, soda, and wood ash combined with wine dregs or water. Such preparations were often left on the hair for several days, and lightened very dark hair to a desirable reddish gold in color. A number of books published during the Renaissance also disclose various formulas for bleaching hair. Typically these compositions were based upon ingredients such as alum, borax, or soda, in combination with plant extracts. It has also been reported that Venetian women obtained their blond hair by sponging it with a solution of soda (or rock alum, black sulfur, and honey) through the hair, spread it over the broad brim of a crownless hat, and let it dry in the sunlight [Cosmetics: Science and Technology, Second Edition, Volume 2, 1972]. This treatment persisted for hundreds of years thereafter, until the fashions changed.

Modern hair bleaches are much milder and non-toxic when compared to their historical counterparts. The key ingredient is a mild oxidizing agent, which is most often hydrogen peroxide. Hydrogen peroxide exerts both a chemical and physical effect on the hair. It is capable of penetrating the hair cuticle and oxidizing the melanin (which provides color) so that the hair becomes noticeably lighter. If treated for a long enough period of time, hair can be colored to very light blonde or white, although it has been said that hair bleached with hydrogen peroxide only may tend to exhibit a yellowish tinge.

Currently, hair bleaches are most commonly found in the two or three component kit form. One component comprises an aqueous based hydrogen peroxide containing solution or emulsion. The second component comprises a powdered bleach composition that contains persulfate salts which act as accelerators of the bleaching process when the two components are combined. The third component, if present, is an alkalizing composition, or a composition that provides alkaline properties. The hydrogen peroxide, persulfates, and, if present, the alkalizing composition, are very reactive when combined, and form nascent oxygen in addition to hydrogen and sodium sulfide. The nascent oxygen greatly facilitates oxidizing and bleaching of melanin from the hair. Typical bleaches generally have a pH of 9 to 11 and are applied to hair for 30 to 60 minutes to achieve the desired results.

Hair bleaches may be used to treat the entire head of hair or only select strands. Highlighting involves application of the bleach composition to only select strands of hair to provide a dappled color effect to the hair. Highlighting is a very popular procedure in both salons and at home. A wide variety of retail highlighting kits are available for purchase by the at home user. Hair products companies make every effort to design the retail kits in the most consumer friendly manner possible to ensure that the at home user has the highest probability of success in obtaining professional quality highlights. The applicator used to the apply the bleach mixture is important in this regard, as is the actual formula for the aqueous oxidizing agent composition, the persulfate composition, and, optionally the bleach oil composition, that are combined to form the bleach mixture.

One common problem with such bleach mixtures is that once they are applied in streaks to the hair, the mixture migrates or diffuses into the surrounding hair shafts. In some cases the streaks initially applied to hair may diffuse so much that they may form one large patch of product on the hair. These large patches result in patches, rather than defined streaks, of highlighted hair and provide a very unprofessional end result. Companies that make and sell hair bleach products are interested in formulating bleach products that exhibit reduced migration or diffusion on the hair, with the end result being more professional looking highlights.

It is an object of the invention to provide a bleach mixture for bleaching or highlighting hair that exhibits reduced migration and diffusion upon application to the hair.

It is a further object of the invention to provide a bleach mixture that provides more professional looking highlights to hair.

It is a further object of the invention to provide a bleach mixture that provides hydrophobically modified particulates in an amount sufficient to cause the mixture to exhibit reduced migration and/or diffusion when applied to the hair.

It is a further object of the invention to provide a method for reducing the diffusion and/or migration of a bleach mixture after it is applied to hair by including one or more hydrophobically modified particulates in the bleach mixture.

It is a further object of the invention to provide a method for improved highlighting of the hair comprising applying to the hair a bleach mixture containing hydrophobically modified particulates that cause reduced migration or diffusion of the bleach composition when it is applied to the hair.

It is a further object of the invention to provide a persulfate bleach composition comprising at least one hydrophobically modified silica.

It is a further object of the invention to provide a kit for bleaching or highlighting hair comprising (a) an aqueous oxidizing agent composition, (b) a persulfate bleach composition containing at least one hydrophobically modified particulate; and, optionally, (c) a bleach oil composition.

SUMMARY OF THE INVENTION

The invention is directed to a hair bleach mixture obtained by combining an aqueous oxidizing agent composition and a persulfate composition, wherein the persulfate composition comprises at least one hydrophobically modified particulate in an amount sufficient to cause reduced diffusion and/or migration of the bleach mixture from the hair strands to which it is applied.

The invention is further directed to a persulfate composition comprising at least one hydrophobically modified particulate.

The invention further comprises a method for reducing the diffusion and/or migration of a bleach mixture after it is applied to the hair, comprising adding to said bleach mixture, obtained by combining an aqueous oxidizing agent composition and a persulfate composition, at least one hydrophobically modified particulate in an amount sufficient to cause reduced diffusion and/or migration of the bleach mixture from the hair strands to which it is applied.

It is a further object of the invention to provide a kit for bleaching or highlighting hair comprising (a) an aqueous oxidizing agent composition, (b) a persulfate bleach composition containing at least one hydrophobically modified particulate; and (c) optionally, a bleach oil composition.

DETAILED DESCRIPTION

I. The Bleach Mixture

The hair bleach composition of the invention is prepared by combining an aqueous oxidizing agent composition, a persulfate composition, and, optionally, a bleach oil (or alkalizing) composition, mixing well, and applying to the hair. The phrase "total mixture" when referred to "by weight of the total mixture" means the mixture obtained by combining the aqueous oxidizing agent composition, the persulfate composition, and, optionally, the bleach oil composition.

A. The Aqueous Oxidizing Agent Composition

The aqueous oxidizing agent composition may be in the solution or emulsion form. If the latter, the emulsion may be in the water-in-oil or oil-in-water form. Further, the emulsion may also be in the microemulsion form, if desired.

When the aqueous oxidizing agent is in the solution form the composition preferably comprises about 1–30% by weight of the total composition of an oxidizing agent, preferably hydrogen peroxide, and about 70–99% by weight of the total aqueous oxidizing agent composition of water. Other water soluble ingredients may be included in the solution, such as humectants, preservatives, water soluble thickeners, antioxidants, and so on.

When the aqueous oxidizing agent composition is in the emulsion form, the composition preferably comprises, by weight of the total aqueous oxidizing agent composition, about 1–30% of oxidizing agent, preferably hydrogen peroxide, about 50–99% water, and about and 0.01–30%, preferably about 0.05–20%, more preferably about 0.1–15% of an oily phase. The aqueous oxidizing agent composition may be in the form of a water-in-oil or oil-in-water emulsion or in the form of a transparent microemulsion wherein the dispersed particles in the continuous phase are so small (generally about 5–1500 Å) that the composition is optically clear. Examples of suitable microemulsion compositions are set forth in U.S. Pat. No. 6,315,989, which is hereby incorporated by reference in its entirety. It is also suitable that the aqueous oxidizing agent composition be in the form of a composition containing liquid crystals as set forth in U.S. Pat. No. 6,238,653, which is hereby incorporated by reference in its entirety.

The various ingredients that may be found in the aqueous oxidizing agent composition (also referred to as "developer") are as follows.

1. Oxidizing Agent.

Preferably the oxidizing agent is hydrogen peroxide, although other suitable peroxides such as urea peroxide, sodium perborate, etc. may be used as well. Preferably the aqueous oxidizing agent composition contains hydrogen peroxide. The oxidizing agent contributes to formation of active oxygen when the various components are combined.

2. Lipophilic Ingredients

If in the emulsion form, the aqueous oxidizing agent composition may contain one or more lipophilic ingredients such as oils, waxes, and the like. If so, suggested ranges are about 1–85%, preferably about 3–70%, preferably about 5–65% by weight of the total aqueous oxidizing agent composition. Suitable lipophilic ingredients may be liquids, semi-solids, or solids oils at room temperature (25° C.). Examples of such lipophilic materials include short chain hydrocarbons, polar hydrophilic oils, fatty acids, fatty alcohols, silicone oils, silicone waxes, and so on.

3. Humectants

Humectants may be present in the aqueous oxidizing agent composition. If so, suggested ranges are from about 0.01–10%, more preferably about 0.05–8%, most preferably about 0.1–5% by weight of the total aqueous oxidizing agent composition of humectant. Suitable humectants include monomeric, homopolymeric, and/or block copolymeric ethers as well as mono-, di-, or polyhydric alcohols.

Suitable ethers are formed by the polymerization of monomeric alkylene oxides, generally ethylene or propylene oxide. Such polymeric ethers have the following general formula:

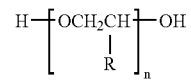

wherein R is H or lower alkyl and n is the number of repeating monomer units, and ranges from 1 to 500.

Also suitable are polyols such as glycerine or $C_{1-4}$ alkylene glycols and the like. Particularly preferred are $C_{1-4}$ alkylene glycols, in particular propylene and/or butylene glycol and ethoxydiglycol.

Suitable mono-, di-, or polyhydric alcohols include glycerin, butylene glycol, ethylene glycol, propylene glycol, and so on.

4. Water Soluble Thickeners

The aqueous oxidizing agent composition may contain one or more water soluble thickeners. If present suggested ranges are from about 0.1–25%, preferably about 0.5–20%, more preferably 1–15% by weight of the total aqueous oxidizing agent composition. Suitable thickeners include, but are not limited to those set forth below.

(a) Acrylic Copolymer Thickeners

Suitable acrylic copolymeric thickeners are comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof. Preferably, the A monomer comprises one or more of acrylic acid or methacrylic acid, and the B monomer comprises is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solids content ranging from about 10–60%, preferably 20–50%, more preferably 25–45% by weight of the polymer, with the remainder water. Preferably, the thickening agent is a polymer comprised of A, B, and C monomers wherein A and B are as defined above, and C has the general formula:

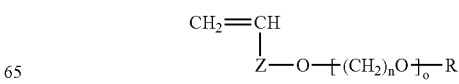

Preferably, in the copolymer used for the secondary thickening agent in the preferred embodiment of the invention, A and B are as above defined; and in the C monomer Z is $(CH_2)_m$, m is 1–2, n is 2, and o is 2–100, and R is a $C_{12-22}$ straight or branched chain alkyl. More preferably in the C monomer m is 1, n is 2, o is 10, and R is $C_{18}$ or stearyl, and the compound is steareth-10 allyl ether/acrylate copolymer, which may be purchased from Allied Colloids under the tradename Salcare SC90 or SL 80.

Also suitable is an aqueous solution of an acrylic polymer comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof. Preferably, the A monomer comprises one or more of acrylic acid or methacrylic acid, and the B monomer comprises is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solids content ranging from about 10–60%, preferably 20–50%, more preferably 25–45% by weight of the polymer, with the remainder water. The composition of the acrylic copolymer may contain from about 0.1–99 parts of the A monomer, and about 0.1–99 parts of the B monomer. Preferably, the acrylic copolymer contains enough of the A monomer to enable ionization in a basic solution, thereby causing the ionized carboxylic acid groups in the polymer to repel each other, and thereby "swallow" water. Particularly preferred acrylic copolymer solutions suitable for use in the developer composition include those sold by Seppic, Inc., under the tradename Capigel, in particular, Capigel 98, which is a white liquid having a pH of 2 to 4, a solids content of about 29–31, a density of 1.04 to 1.08, and a viscosity of 700–1000 millipascal seconds at 25° C.

(b) Associative Thickeners

Various other types of associative thickeners may be present, including water soluble urethane homo- and copolymers, and the like.

4. Nonionic Surfactants

If desired, the aqueous oxidizing agent composition may contain one or more nonionic surfactants. Recommended ranges are 0.01–10%, preferably 0.05–8%, more preferably 0.1–7% by weight of the total aqueous oxidizing agent composition.

(a) Alkoxylated Alcohols

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Particularly preferred is Ceteareth 20, which is the reaction product of a mixture of cetyl and stearyl alcohol with ethylene oxide, and the number of repeating ethylene oxide units in the molecule is 20.

(b) Alkoxylated Carboxylic Acids

Also suitable as the nonionic surfactant are alkyoxylated carboxylic acids, which are formed by the reaction of a carboxylic acid with an alkylene oxide or with a polymeric ether. The resulting products have the general formula:

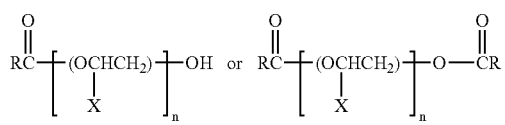

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1–100.

(c) Sorbitan Derivatives

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

The aqueous oxidizing agent composition may also comprise a variety of other ingredients including cationic, amphoteric, or zwitterionic surfactants, preservatives.

B. The Persulfate Composition

The persulfate composition may be in the cream or free-flowing particulate form, and contains at least one particulate that under normal circumstances would be a "gelling particulate" e.g. when combined with water would cause a viscosity increase or gellation of the water phase because of its hydrophilic character, but where such particulate has been hydrophobically modified (e.g. reacted with hydrophobic substitutents) to a degree sufficient such that its gelling capability will be reduced or completely eliminated upon contact with aqueous media. The persulfate composition comprises ingredients such as those set forth below:

1. Persulfates

The persulfate composition comprises one or more of various alkaline earth metal, alkali metal, or ammonium persulfate compounds that exhibit oxidizing activity (generating active oxygen) when combined with the aqueous oxidizing agent composition. Preferably such persulfates comprise one or more of an alkali metal, alkaline earth metal, or ammonium persulfate. Examples of alkali metal persulfates include lithium, sodium, potassium, cesium, and the like. Examples of suitable alkaline earth metals include magnesium, calcium, and the like. Particularly preferred are sodium, potassium, and ammonium persulfates. The persulfates are generally in particulate form, have particle sizes ranging from about 0.1 to 200 microns, and are present in amounts ranging from about 0.01–95%, preferably about 3–75%, more preferably about 5–65% by weight of the total persulfate composition. The persulfates are reactive with the hydrogen peroxide or other peroxide oxidizing agent present and when the persulfate composition and aqueous oxidizing agent composition, and optionally the bleach oil composition are combined, nascent, free oxygen is generated.

2. Alkalizing Agents

The persulfate composition preferably contains one or more alkalizing agents, including inorganic salts such as aluminum, sodium, potassium, and magnesium salts of inorganic or organic acids. Examples of suitable salts include alkali metal and alkaline earth metal silicates, sodium metasilicate, sodium chloride, sodium silicate, aluminum citrate, calcium saccharin, calcium salicylate, calcium citrate, calcium benzoate, magnesium acetate, magnesium ascorbate, magnesium PCA, magnesium gluconate, potassium acetate, potassium benzoate, potassium citrate, potassium sorbate, sodium acetate, sodium ascorbate, sodium silicate, sodium citrate, sodium gluconate, sodium pyruvate, and mixtures thereof. Particularly preferred inorganic sales are sodium silicate, sodium metasilicate, or mixtures thereof. Alkalizing agents may be present in the composition ranging from about 0.1–30%, preferably 0.5–25%, more preferably from about 1–20% by weight of the total composition.

3. Particulate Fillers

The persulfate composition also preferably comprises one or more particulate fillers. Preferably, the persulfate composition comprises about 5–60%, preferably about 8–55%, more preferably about 10–50% by weight of the total persulfate composition of the particulate fillers. The term "particulate filler" means a generally inert particulate having a particle size of about 0.1–250 microns. The particulate fillers provide volume and improved flow properties and, when mixed with the persulfates, dilute the persulfate particles. Preferred is where the hydrophobically modified particulate is a particulate filler. In particular, one or more of the particulate fillers may also provide gelling capability to the composition, such that when combined with the aqueous oxidizing agent composition the particulates will cause the mixture to gel, or thicken, upon standing. However, one or more of those same particulate fillers may be hydrophobically modified to a degree sufficient to cause the particulate to become hydrophobic and there reduce or eliminate the gelling capability of that particulate. At the same time such hydrophobic particulate will provide a hydrophobic barrier when applied to hair, thereby preventing or reducing the tendency of the bleach mixture applied to the hair to spread or diffuse.

A variety of particulate fillers are suitable including inorganics, inorganic salts, hydrophilic colloids, carbohydrates, soaps, alkyl sulfates, and the like.

(a) Inorganics

Examples of inorganics include silica, hydrated silica, alumina, attapulgite, bentonite, calcium oxide, chalk, diamond powder, diatomaceous earth, fuller's earth, hectorite, kaolin, mica, magnesium oxide, magnesium peroxide, montmorillonite, pumice, talc, tin oxide, zeolite, zinc oxide, and the like. One or more of the inorganics present in the composition may be hydrophobically modified to a degree sufficient such that the particulate exhibits reduced or eliminated capability to gel the bleach mixture that is formed by combining the aqueous oxidizing agent composition with the persulfate composition. In the preferred embodiment of the invention, one or more of the inorganics present are hydrophobically modified to a degree sufficient to reduce or eliminate the gelling capability of the particulate. In the most preferred embodiment of the invention, the silica is hydrophobically modified by replacing some of the hydroxyl groups on the surface of the fumed silica with trimethylsiloxy groups to provide an ingredient referred to as silica silylate. Another modified silica may be prepared by modifying the surface of fumed silica by adding dimethyl silyl groups to provide an ingredient referred to as silica dimethylsilylate. Another suitable hydrophobically modified silica is silica dimethicone silylate, obtained by modifying the surface of fumed silica by coating or reacting with dimethicone.

(b) Hydrophilic Colloids or Polymers

Examples of suitable hydrophilic colloids include hydroxyethylcellulose, locust bean gum, maltodextrin, methylcellulose, agar, dextran, dextran sulfate, gelatin, pectin, potassium alginate, sodium carboxymethylchitin, xanthan gum, and the like. If desired, one or more of the hydrophilic colloids may be particulates, and may further be hydrophobically modified to provide ingredients that exhibit a reduced or completely eliminated tendency to gel the mixture when the aqueous oxidizing agent composition and persulfate composition are mixed. In addition, the hydrophobically modified materials will provide a hydrophobic barrier when applied to the hair, which prevents bleeding of the bleach mixture when it is applied in streaks to the hair. In this case, the cellulosics may be reacted with long chain alkyl groups (C6–30), butoxy, propoxy, silicones, or silicone substituted polymers to provide hydrophobic character. Examples of such modified ingredients include carboxymethylcellulose, carboxyethylcellulose, and so on.

(c) Carbohydrates

Examples of suitable carbohydrates include sugars such as glucose, sucrose, maltose, xylose, trehelose, and derivatives thereof, in particular sugar esters of long chain, $C_{14-30}$ fatty acids, as well as dextrins and derivatives thereof.

(d) Soaps and Alkyl Sulfates

Examples of soaps and alkyl sulfate particles that may act as particulate fillers include the aluminum, sodium, and potassium salts of fatty acids such as aluminum distearate, aluminum isostearate, aluminum myristate, calcium behenate, calcium stearate, calcium behenate, magnesium stearate, magnesium tallowate, potassium palmitate, potassium stearate, potassium oleate, sodium stearate, sodium oleate, sodium myristate, sodium palmitate, and the like. Suitable alkyl sulfates include sodium lauryl sulfate, sodium cetyl sulfate, sodium myristyl sulfate, sodium octyl sulfate, and the like.

4. Inorganic Colorants

If desired, the persulfate composition may comprise about 0.01–2%, preferably about 0.05–1%, more preferably about 0.1–1% by weight of the total persulfate composition of an inorganic colorant. The inorganic colorant is preferably in the particulate form and will provide a subtle coloration to the powder composition to make it more aesthetically pleasing for commercial purposes. Particularly preferred for use in the bleach composition is ultramarine blue.

C. The Bleach Oil Composition

The third optional component that may optionally be used to prepare the mixture applied to hair is a bleach oil (or alkalizing) composition. The term "bleach oil composition" means a liquid composition that is mixed with the aqueous oxidizing agent composition and the persulfate composition to provide a mixture suitable for bleaching or highlighting hair. Generally the bleach oil composition will contain one or more ingredients that are capable of conditioning hair and ameliorating the drying effects that bleaches sometimes have on hair.

The bleach oil composition is preferably in the emulsion form, and may be a water-in-oil or oil-in-water emulsion or microemulsion. The bleach oil composition generally comprises about 1–75%, preferably about 2–70%, more preferably about 5–65% by weight of the total composition of water, and about 0.1–50%, preferably about 0.5–45%, more preferably about 1–40% by weight of the total composition of lipophilic ingredients. These lipophilic ingredients are as mentioned above with respect to the aqueous oxidizing agent and/or persulfate composition. In addition, the bleach oil composition may comprise other ingredients such as surfactants, alkalizing agents, antioxidants, humectants, other lipophilic ingredients, all in the amounts taught above with respect to the aqueous oxidizing agent composition. Additionally, the bleach oil may be found in the microemulsion form wherein the dispersed particles in the emulsion exhibit a small particle size, e.g. from about 5 to 1500 Å.

III. The Method

The oxidizing agent composition and the persulfate composition and, optionally, the bleach oil composition are combined in sufficient ratios to yield a mixture that is capable of bleaching hair when applied thereto. Generally, in the preferred embodiment of the invention, the bleach mixture comprises about 20–80% by weight of the total mixture of the aqueous oxidizing agent composition, about 5–40% by weight of the total mixture of persulfate composition, and, optionally, about 5–30% by weight of the total mixture of the bleach oil composition.

The composition applied to the hair will exhibit reduced migration and/or diffusion from the hair strands to which it is applied. The bleach mixture may be applied to the hair with any number of application devices which are capable of depositing the bleach mixture in the desired pattern on the hair strands. Because the bleach mixture will not readily migrate or diffuse from the hair strands to which it is applied, the resulting highlights look more professional.

III. The Kit

The invention also comprises a kit for bleaching or highlighting hair comprising: (a) an aqueous oxidizing agent composition; and (b) a persulfate composition containing at least one hydrophobically modified particulate in an amount sufficient such that the mixture of compositions (a) and (b) are applied to the hair the mixture exhibits reduced migration and/or diffusion from the hair strands to which it is applied. The kit may also contain a bleach oil composition, and if desired, a hair conditioner composition usually found in a packette form. Where the kit is used to apply highlights to hair, there is also an applicator for use in applying the bleach mixture to the hair. A variety of applicators may be used so long as they are capable of providing streaks or deposits of bleach mixture to the hair in the desired pattern.

The invention will be further described in connection with the following examples, that are set forth for the purposes of illustration only.

EXAMPLE 1

An aqueous oxidizing agent composition (or developer) was made according to the following formula:

|  | w/w % |
| --- | --- |
| Water | QS |
| EDTA | 0.02 |
| Propylene glycol | 5.00 |
| Laureth 23 | 1.50 |
| Cetearyl alcohol/sodium lauryl sulfate/sodium cetearyl sulfate | 1.50 |
| Cetearyl alcohol | 1.00 |
| Hydrogen peroxide (35% aqueous solution) | 26.00 |
| Phosphoric acid | 0.02 |

-continued

|  | w/w % |
| --- | --- |
| Disodium phosphate | 0.05 |
| Steareth-10 allyl ether/acrylates copolymer | 0.05 |

A powdered persulfate composition was made according to the following formula:

|  | w/w % |
| --- | --- |
| Potassium persulfate | 38.50 |
| Sodium persulfate | 14.50 |
| Ammonium persulfate | 9.00 |
| Sodium metasilicate | 11.00 |
| Sodium chloride | 7.00 |
| Sucrose | 6.00 |
| Ultramarines | 0.25 |
| Ammonium chloride | 4.00 |
| Silica | 1.00 |
| Sodium lauryl sulfate | 1.00 |
| Disodium EDTA | 1.00 |
| Silica silylate | 1.00 |
| Hydroxyethylcellulose | 3.00 |
| Xanthan gum | 2.75 |

A bleach oil composition made according to the following formula:

|  | w/w % |
| --- | --- |
| Water | 20.60 |
| Tetrasodium EDTA | 0.80 |
| Isopropanol amine | 10.00 |
| Ethoxydiglycol | 8.00 |
| Laureth 4 | 15.00 |
| Oleic acid | 13.00 |
| Ethanolamine | 3.00 |
| Isopropyl myristate | 9.50 |
| Coconut oil | 5.00 |
| Ammonium hydroxide | 13.00 |
| Fragrance | 1.00 |
| Hydrolyzed marine collagen | 0.50 |
| Wheat amino acids | 0.50 |
| Sodium benzotriazolyl sulfonate/buteth 3/Tributyl citrate | 0.10 |

The preferred mixture to be applied to the hair was prepared by combining 4 parts of the aqueous oxidizing agent composition and 1 part of the persulfate composition and mixing well. The composition was a whitish liquid that gelled to a slightly more viscous liquid upon standing.

In another embodiment of the invention a bleach mixture was prepared by combining 28.5 grams bleach oil, 123.5 grams of the aqueous oxidizing agent composition, and 47.5 grams of the persulfate composition and mixing well.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A hair bleach mixture obtained by combining an aqueous oxidizing agent composition and a persulfate composition comprising at least one hydrophobically modified particulate, said hydrophobically modified particulate being present in the mixture in an amount sufficient to reduce diffusion and/or migration of the mixture from the hair strands to which it is applied.

2. The mixture of claim 1 wherein the hydrophobically modified particulate comprises a particulate filler.

3. The mixture of claim 2 wherein the amount of hydrophobically modified particulate filler in the persulfate composition ranges from about 0.01 to 60% by weight of the total persulfate composition.

4. The mixture of claim 3 wherein the persulfate composition additionally comprises, by weight of the total persulfate composition, from about 1–95% of one or more persulfates.

5. The mixture of claim 4 wherein the persulfates are ammonium, sodium, potassium, and mixtures thereof.

6. The mixture of claim 2 wherein the hydrophobically modified particulate filler is an inorganic, hydrophobically modified hydrophilic colloid, or mixtures thereof.

7. The mixture of claim 2 wherein the hydrophobically modified particulate filler comprises one or more hydrophobically modified inorganics.

8. The mixture of claim 7 wherein the hydrophobically modified inorganic is silica silylate, silica dimethylsilylate, silica dimethicone silylate, or mixtures thereof.

9. The mixture of claim 6 wherein the hydrophobically modified particulate filler is a hydrophobically modified hydrophilic colloid.

10. The mixture of claim 9 wherein the hydrophobically modified hydrophilic colloid is a cellulose modified with propoxy, butoxy, silicone, or C6–30 alkyl groups; or a hydrophobic polymer.

11. The mixture of claim 1 wherein the aqueous oxidizing agent composition comprises, by weight of the total aqueous oxidizing agent composition, from about 1–30% oxidizing agent and 70–99% water.

12. The mixture of claim 11 wherein the aqueous oxidizing agent composition additionally comprises from about 1–85% of one or more lipophilic ingredients.

13. The mixture of claim 11 wherein the aqueous oxidizing agent composition comprises from about 0.01–10% of one or more humectants.

14. The mixture of claim 11 wherein the aqueous oxidizing agent composition comprises from about 0.1–25% by weight of the total aqueous oxidizing agent composition of one or more water soluble thickeners.

* * * * *